US006790644B2

(12) United States Patent
Straganz et al.

(10) Patent No.: US 6,790,644 B2
(45) Date of Patent: Sep. 14, 2004

(54) 1,3-DICARBONYL-DIOXYGENASE—A NEW C-C-BOND CLEAVING ENZYME

(75) Inventors: Grit Straganz, Lienz (AT); Anton Glieder, Gleisdorf (AT); Lothar Brecker, Herdecke (DE)

(73) Assignee: Biocatalytics, Inc., Pasadena, CA (US)

( * ) Notice: Subject to any disclaimer, the term of this patent is extended or adjusted under 35 U.S.C. 154(b) by 0 days.

(21) Appl. No.: 10/141,225

(22) Filed: May 7, 2002

(65) Prior Publication Data

US 2003/0148487 A1 Aug. 7, 2003

Related U.S. Application Data

(60) Provisional application No. 60/328,228, filed on Oct. 9, 2001.

(51) Int. Cl.[7] ............................. C12N 9/02; C12N 1/20; C12N 15/00; C07H 21/02; C07H 21/04
(52) U.S. Cl. ................. 435/189; 435/252.3; 435/320.1; 435/71.1; 435/440; 536/23.2; 536/23.1
(58) Field of Search ..................... 435/189, 252.3, 435/320.1, 440, 71.1, 190, 6; 536/23.2, 23.1

(56) References Cited

PUBLICATIONS

Mathematical modeling of growth and product formation by Acinetobacter johnsonii in a multiple substrate environment T. Mandl, A. Raninger, W. Steiner Biotechnology 2000, DECHEMA Annual Meeting on Biotechnology, Berlin, Germany, Sep. 3–8, 2000.

Optimal fed–batch feeding strategies for enzyme production with Acinetobacter johnsonii T. Mandl, G. Straganz, W. Steiner Biotechnology 2000, DECHEMA Annual Meeting on Biotechnology, Berlin, Germany, Sep. 3–8, 2000.

T. Mandl, W. Steiner "Reaktionstechnische Untersuchungen zur Optimierung der Produktion spezieller b–Ketolasen in Acinetobacter johnsonii" OEGBT Jahrestagung 2000, Seggau, Austria, Apr. 27–28, 2000 (English translation attached).

Balzer, D. et al., "KorB protein of promiscuous plasmid RP4 recognizes inverted sequence repetitions in regions essential for conjugative plasmid transfer." *Nucleic Acids Research* 20(8):1851–1858 (1992).

*Primary Examiner*—P. Achutamurthy
*Assistant Examiner*—Yong D. Pak
(74) *Attorney, Agent, or Firm*—Fulbright & Jaworski

(57) ABSTRACT

An enzyme that cleaves 1,3-dicarbonyl compounds by incorporating molecular oxygen into the substrate in amounts equimolar to the amount of substrate cleaved. The enzyme from *Acinetobacter johnsonii* is a multimer of about 67 kilodaltons made up of subunits of about 16.6 kilodaltons. Nucleotide and amino acid sequence analysis of a cloned *A. johnsonii* subunit indicates little homology with other proteins. Native or recombinant enzyme can be used to decontaminate or detoxify acetylacetone or related diketones.

15 Claims, 5 Drawing Sheets

```
  1 TCAGCAAAAGATAGATCGTTTTTTTTATGAAAGAAATCTATTGTTCTATATATTTTTGTAGTTCATTTTTAAGCAAACACTTGTGCGTTT   90
                                                                            ORF: Dioxygenase →
 91 TTAGACAATTTTCCAAATCTCATTTCAATATTATGAAGATGTGTCATGTGTAGACACACATATAAGGAGATATGAAATGGATTATTGTAA  180
                                                                               M  D  Y  C  N
181 TAAAAAACACACTGCTGAAGAATATGTAAAAATTTCAGATAATAACTATGTTCCTTTCCCAGAAGCATTTTCTGATGGTGGAATCACTTG  270
     K  K  H  T  A  E  E  Y  V  K  I  S  D  N  N  Y  V  P  F  P  E  A  F  S  D  G  G  I  T  W
271 GCAATTATTACATTCCTCACCAGAAACAAGTAGTTGGACGGCAATTTTCAACTGTCCTGCTGGCTCATCTTTTGCTTCTCATATTCATGC  360
     Q  L  L  H  S  S  P  E  T  S  S  W  T  A  I  F  N  C  P  A  G  S  S  F  A  S  H  I  H  A
361 TGGCCCCGGTGAATATTTCCTGACTAAGGGAAAAATGGAAGTGCGTGGTGGCGAGCAAGAGGGTGGTAGCACTGCTTATGCACCAAGCTA  450
     G  P  G  E  Y  F  L  T  K  G  K  M  E  V  R  G  G  E  Q  E  G  G  S  T  A  Y  A  P  S  Y
451 CGGTTTTGAATCTTCAGGTGCATTGCATGGTAAAACTTTCTTTCCTGTCGAAAGCCAGTTCTATATGACCTTTTTAGGGCCGCTTAATTT  540
     G  F  E  S  S  G  A  L  H  G  K  T  F  F  P  V  E  S  Q  F  Y  M  T  F  L  G  P  L  N  F
541 TATTGATGATAACGGAAAAGTTATTGCATCGATTGGTTGGGCTGAAGCTCAAGGTGCATGGTTAGCTACCAAAAATGAGGCTGCCTGACT  630
     I  D  D  N  G  K  V  I  A  S  I  G  W  A  E  A  Q  G  A  W  L  A  T  K  N  E  A  A  *
```

*(Amino-acid-sequence:*
```
M D Y C N K K H T A E E Y V K I S D N N Y V P F P E A
F S D G G I T W Q L L H S S P E T S S W T A I F N C P
A G S S F A S H I H A G P G E Y F L T K G K M E V R G
G E Q E G G S T A Y A P S Y G F E S S G A L H G K T F
F P V E S Q F Y M T F L G P L N F I D D N G K V I A S
I G W A E A Q G A W L A T K N E A A
```

*Nucleotide-sequence:*
```
TCAGCAAAAGATAGATCGTTTTTTTTATGAAAGAAATCTATTGTTCTATATATTTTTGTAGTTCATTTTTAAGCAAACACTTGTGCGTTT
TTAGACAATTTTCCAAATCTCATTTCAATATTATGAAGATGTGTCATGTGTAGACACACATATAAGGAGATATGAAATGGATTATTGTAA
TAAAAAACACACTGCTGAAGAATATGTAAAAATTTCAGATAATAACTATGTTCCTTTCCCAGAAGCATTTTCTGATGGTGGAATCACTTG
GCAATTATTACATTCCTCACCAGAAACAAGTAGTTGGACGGCAATTTTCAACTGTCCTGCTGGCTCATCTTTTGCTTCTCATATTCATGC
TGGCCCCGGTGAATATTTCCTGACTAAGGGAAAAATGGAAGTGCGTGGTGGCGAGCAAGAGGGTGGTAGCACTGCTTATGCACCAAGCTA
CGGTTTTGAATCTTCAGGTGCATTGCATGGTAAAACTTTCTTTCCTGTCGAAAGCCAGTTCTATATGACCTTTTTAGGGCCGCTTAATTT
TATTGATGATAACGGAAAAGTTATTGCATCGATTGGTTGGGCTGAAGCTCAAGGTGCATGGTTAGCTACCAAAAATGAGGCTGCCTGACT)
```

Figure 4

SEQUENCE LISTING

<160> NUMBER OF SEQ ID NOS: 12

<210> SEQ ID NO 1
<211> LENGTH: 459
<212> TYPE: DNA
<213> ORGANISM: Acinetobacter johnsonii

<400> SEQUENCE: 1

```
atggattatt gtaataaaaa acacactgct gaagaatatg taaaaatttc agataataac      60
tatgttcctt tcccagaagc attttctgat ggtggaatca cttggcaatt attacattcc     120
tcaccagaaa caagtagttg gacggcaatt ttcaactgtc ctgctggctc atcttttgct     180
tctcatattc atgctggccc cggtgaatat ttcctgacta agggaaaaat ggaagtgcgt     240
ggtggcgagc aagagggtgg tagcactgct tatgcaccaa gctacggttt tgaatcttca     300
ggtgcattgc atggtaaaac tttctttcct gtcgaaagcc agttctatat gaccttttta     360
gggccgctta attttattga tgataacgga aaagttattg catcgattgg ttgggctgaa     420
gctcaaggtg catggttagc taccaaaaat gaggctgcc                            459
```

<210> SEQ ID NO 2
<211> LENGTH: 153
<212> TYPE: PRT
<213> ORGANISM: Acinetobacter johnsonii

<400> SEQUENCE: 2

```
Met Asp Tyr Cys Asn Lys Lys His Thr Ala Glu Glu Tyr Val Lys Ile
  1               5                  10                  15

Ser Asp Asn Asn Tyr Val Pro Phe Pro Glu Ala Phe Ser Asp Gly Gly
             20                  25                  30
```

```
Ile Thr Trp Gln Leu Leu His Ser Ser Pro Glu Thr Ser Ser Trp Thr
         35                  40                  45

Ala Ile Phe Asn Cys Pro Ala Gly Ser Ser Phe Ala Ser His Ile His
 50                  55                  60

Ala Gly Pro Gly Glu Tyr Phe Leu Thr Lys Gly Lys Met Glu Val Arg
 65                  70                  75                  80

Gly Gly Glu Gln Glu Gly Gly Ser Thr Ala Tyr Ala Pro Ser Tyr Gly
                 85                  90                  95

Phe Glu Ser Ser Gly Ala Leu His Gly Lys Thr Phe Phe Pro Val Glu
                100                 105                 110

Ser Gln Phe Tyr Met Thr Phe Leu Gly Pro Leu Asn Phe Ile Asp Asp
                115                 120                 125

Asn Gly Lys Val Ile Ala Ser Ile Gly Trp Ala Glu Ala Gln Gly Ala
130                 135                 140

Trp Leu Ala Thr Lys Asn Glu Ala Ala
145                 150
```

<210> SEQ ID NO 3
<211> LENGTH: 36
<212> TYPE: DNA
<213> ORGANISM: Acinetobacter johnsonii
<220> FEATURE:
<221> NAME/KEY: source
<222> LOCATION: (1)..(8)
<223> OTHER INFORMATION: synthetic sequence

<400> SEQUENCE: 3
ctatacatat ggattattgt aataaaaaac acactg                                 36

<210> SEQ ID NO 4
<211> LENGTH: 29
<212> TYPE: DNA
<213> ORGANISM: Acinetobacter johnsonii

<400> SEQUENCE: 4
gacaagcttc ggatttcctc caatccacg                                         29

<210> SEQ ID NO 5
<211> LENGTH: 18
<212> TYPE: PRT
<213> ORGANISM: Acinetobacter johnsonii
<220> FEATURE:
<221> NAME/KEY: MISC_FEATURE
<222> LOCATION: (2)..(2)
<223> OTHER INFORMATION: Ile or Leu
<220> FEATURE:
<221> NAME/KEY: MISC_FEATURE
<222> LOCATION: (5)..(5)
<223> OTHER INFORMATION: Ile or Leu
<220> FEATURE:
<221> NAME/KEY: MISC_FEATURE
<222> LOCATION: (15)..(15)
<223> OTHER INFORMATION: Ile or Leu

<400> SEQUENCE: 5

```
Val Xaa Ala Ser Xaa Gly Trp Ala Glu Ala Gln Gly Ala Trp Xaa Ala
 1               5                  10                  15

Thr Lys
```

<210> SEQ ID NO 6
<211> LENGTH: 12
<212> TYPE: PRT
<213> ORGANISM: Acinetobacter johnsonii
<220> FEATURE:

```
<221> NAME/KEY: MISC_FEATURE
<222> LOCATION: (6)..(6)
<223> OTHER INFORMATION: Ile or Leu
<220> FEATURE:
<221> NAME/KEY: MISC_FEATURE
<222> LOCATION: (9)..(9)
<223> OTHER INFORMATION: Ile or Leu
<220> FEATURE:
<221> NAME/KEY: MISC_FEATURE
<222> LOCATION: (12)..(12)
<223> OTHER INFORMATION: Ile or Leu

<400> SEQUENCE: 6

Lys Gly Asn Asp Asp Xaa Phe Asn Xaa Pro Gly Xaa
1               5                   10

<210> SEQ ID NO 7
<211> LENGTH: 24
<212> TYPE: PRT
<213> ORGANISM: Acinetobacter johnsonii
<220> FEATURE:
<221> NAME/KEY: MISC_FEATURE
<222> LOCATION: (21)..(21)
<223> OTHER INFORMATION: Ile or Leu

<400> SEQUENCE: 7

Asn Glu Gln Glu Gly Gly Ser Thr Ala Tyr Ala Pro Ser Tyr Gly Phe
1               5                   10                  15

Glu Ser Ser Gln Xaa His Gly Lys
            20

<210> SEQ ID NO 8
<211> LENGTH: 51
<212> TYPE: DNA
<213> ORGANISM: Artificial Sequence
<220> FEATURE:
<223> OTHER INFORMATION: degenerate oligonucleotide
<220> FEATURE:
<221> NAME/KEY: misc_feature
<222> LOCATION: (33)..(33)
<223> OTHER INFORMATION: a or g or c or t

<400> SEQUENCE: 8
aaygarcarg arggvggvtc dacmgcwtay gcnccwtcdt ayggvttyga a            51

<210> SEQ ID NO 9
<211> LENGTH: 24
<212> TYPE: DNA
<213> ORGANISM: Artificial Sequence
<220> FEATURE:
<223> OTHER INFORMATION: degenerate oligonucleotide
<220> FEATURE:
<221> NAME/KEY: misc_feature
<222> LOCATION: (4)..(4)
<223> OTHER INFORMATION: a or g or c or t

<400> SEQUENCE: 9
ccangckccy tgvgcytcvg ccca                                         24

<210> SEQ ID NO 10
<211> LENGTH: 20
<212> TYPE: DNA
<213> ORGANISM: Acinetobacter johnsonii

<400> SEQUENCE: 10
tcttcaggtg cattgcatgg                                              20

<210> SEQ ID NO 11
```

```
-continued

<211> LENGTH: 20
<212> TYPE: DNA
<213> ORGANISM: Acinetobacter johnsonii

<400> SEQUENCE: 11
accatgcaat gcacctgaag                                                  20

<210> SEQ ID NO 12
<211> LENGTH: 630
<212> TYPE: DNA
<213> ORGANISM: Acinetobacter johnsonii

<400> SEQUENCE: 12
tcagcaaaag atagatcgtt tttttttatga aagaaatcta ttgttctata tattttttgta      60 gttcatttt  aagcaaacac ttgtgcgttt ttagacaatt ttccaaatct catttcaata     120
ttatgaagat gtgtcatgtg tagacacaca tataaggaga tatgaaatgg attattgtaa     180
taaaaaacac actgctgaag aatatgtaaa aatttcagat aataactatg ttcctttccc     240
agaagcattt tctgatggtg gaatcacttg gcaattatta cattcctcac cagaaacaag     300
tagttggacg gcaattttca actgtcctgc tggctcatct tttgcttctc atattcatgc     360
tggccccggt gaatatttcc tgactaaggg aaaaatggaa gtgcgtggtg gcgagcaaga     420
gggtggtagc actgcttatg caccaagcta cggtttttgaa tcttcaggtg cattgcatgg     480
taaaactttc tttcctgtcg aaagccagtt ctatatgacc tttttagggc cgcttaattt     540
tattgatgat aacggaaaag ttattgcatc gattggttgg gctgaagctc aaggtgcatg     600
gttagctacc aaaaatgagg ctgcctgact                                      630
```

1,3-DICARBONYL-DIOXYGENASE— A NEW C-C-BOND CLEAVING ENZYME

CROSS REFERENCE TO RELATED APPLICATIONS

This application is based on provisional application No. 60/328,228, filed on Oct. 9, 2001.

FIELD OF INVENTION

This invention relates generally to the field of biochemistry, in particular to the isolation, cloning and expression of 1,3-dicarbonyl-dioxygenase.

BACKGROUND

Acetylacetone (synonyms: 2,4-Pentanedione, CAS No. 123-54-6; pentane-2,4-dione) is a widely used volatile industrial chemical. Studies of repeated exposure by peroral and inhalation routes have shown acute toxicity (Ballantyne B, Dodd D E, Myers R C, Nachreiner D J. 1986. Drug Chem Toxicol 9(2):133–46) including central neurotoxicity (Graham R H, Dodd D E. Ballantyne B. 2001. Vet Hum Toxicol 43(1):14–8) and possible immune system toxicity (Ballantyne B, et al. 1986, supra). Furthermore, fetotoxicity was observed (Tyl R W, Ballantyne B, Pritts I M, Garman R H, Fisher L C, France K A, McNeil D J. 1990. Toxicol Ind Health 6(3-4):461–74). The well characterized toxicology has made it a model compound for in vitro toxological investigations (Schmuck G, Schluter, G. 1996. Toxicol Ind Health 12(5):683–96).

On the other hand, diacylmethanes such as acetylacetone and derivatives have been shown to inhibit the mutagenic effect of various mutagenic substrates. As has been demonstrated in the model mechanism *Salmonella typhimurium*, acetylacetone, benzoylacetone and dibenzoylmethane inhibit the mutagenicity of 2-naphthohydroxamic acid; dibenzoylmethane and 1,3-indandione inhibit that of methylnitrosourea, benzo[a]pyrene and aflatoxin B1. The binding to tRNA of benzo[a]pyrene and aflatoxin B1 is inhibited by (a) benzoylacetone and dibenzoylmethane; and (b) dibenzoylmethane, 1,3-indandione and 1,1,1-trifluoroacetylacetone, respectively (Wang C Y, Lee M S, Zukowski K. 1991. Mutat Res 262(3):189–93). In the case of methylnitrosourea, a concomitant exposure to the inhibitors and the mutagen is necessary. These results demonstrate that active methylene compounds can inhibit mutagenicity and nucleic acid-binding of chemical carcinogens, presumably by trapping carcinogenic electrophiles, and can be potential anti-carcinogenic agents during the initiation stage.

Enzymes that cleave acetylacetone provide a means to reduce environmental contamination and acute toxicity of acetylacetone. Various enzymes acting on acetylacetone and other diketones have been previously described. One such enzyme from Pseudomonas sp. Strain VM15C hydrolyses acetylacetone to acetate and acetone (Sakai, K., Hamada, N., Watanabe, Y. 1985: Agric. Biol. Chem 49:1901–1902; and Sakai, K., Hamada, N., Watanabe, Y. 1986. Agric. Biol. Chem. 50:989–996). Although acetate can be easily utilized by the cell, acetone is not as easily introduced into metabolic pathways.

Several other enzymes, including acetylpyruvate hydrolase, catalyze the hydrolytic cleavage of beta-diketones. However, these enzymes are restricted to oxo-acid substrates and cannot cleave acetylacetone (Davey, J. F., Ribbons, D. W. 1975. J. Biol. Chem. 250:3826–3830; and Watson, G. K., Houghton, C., Cain, R. B. 1974. Biochem. J. 140:277–292).

Multi-step enzyme reactions not involving hydrolytic cleavage of acetylacetone are a possible means of acetylacetone degradation For example, a terminal oxidation step catalyzed by a cofactor-dependent monooxygenase, as is known for long-chain aliphatic hydrocarbon degradation (Gottschalk G., Bacterial Metabolism, Springer,1986), would result in a primary alcohol, which could be further oxidized to acetylpyruvic acid and integrated into the fatty acid degradation pathway. Also, subterminal oxidation, inserting an oxygen into acetylacetate by a monooxygenase in a Bayer-Villiger-like reaction, would give acetic-acid-2-oxo-ethyl-ester, which could be further hydrolyzed (Gottschalk G., 1986, supra; and Whyte L G, Hawari J, Zhou E, Bourbonniere L, Inniss W E, Greer C W. 1998. Appl Environ Microbiol 64(7):2578–84). However, cofactor-dependent multi-step enzyme reactions are relatively complicated detoxification systems.

For the foregoing reasons, there is a need for an enzyme capable of cleaving acetylacetone and related diketones to easily metabolized products in a single step.

SUMMARY

The present invention provides a purified enzyme exhibiting 1,3-dicarbonyl-dioxygenase activity. In a preferred embodiment, the enzyme is purified from a strain of *Acinetobacter johnsonii* capable of growing on acetylacetone as the sole carbon source. In a most preferred embodiment, the isolated *A. johnsonii* enzyme is a multimeric protein of about 67 kilodaltons having subunits of about 16.6 kilodaltons.

The present invention provides an isolated polypeptide subunit of 1,3-dicarbonyl-dioxygenase. In a preferred embodiment, the subunit comprises the amino acid sequence set forth in SEQ ID NO: 2. Subunits comprising amino acid sequences having at least 70% sequence identity to SEQ ID NO: 2, determined by BLAST analysis, are included within the scope of the invention.

The present invention also provides an isolated polynucleotide encoding the amino acid sequence set forth in SEQ ID NO: 2. A preferred embodiment comprises the nucleotide sequence set forth in SEQ ID NO: 1. Other embodiments include a polynucleotide encoding an amino acid sequence that is at least 70% identical to SEQ ID NO: 2, and a polynucleotide comprising a nucleotide sequence that is at least 60% identical to SEQ ID NO: 1. Sequence identity is determined by BLAST analysis.

The present invention further includes polynucleotides encoding 1,3-dicarbonyl-dioxygenase subunits in which the polynucleotide comprises one of the nucleotide sequences set forth in SEQ ID NOs: 3, 4, 8, 9, 10 and 11.

The present invention provides a vector containing the polynucleotide sequences described herein. Also provided are host cells containing a vector of this invention. Host cells can be mammalian cells, plant cells, insect cells, yeast and other fungi, or bacteria.

The present invention provides a process for producing a 1,3-dicarbonyl-dioxygenase. The process includes culturing a cell expressing the enzyme under appropriate conditions for producing the enzyme, and isolating the enzyme from the cell culture. The cell can be any cell expressing the enzyme. In a preferred embodiment, the cell is from a strain of *A. johnsonii*. In another preferred embodiment, the cell is a host cell containing a vector of this invention.

The present invention also provides a process for producing a subunit of a 1,3-dicarboryl-dioxygenase. The steps include culturing a cell expressing the subunit under appropriate conditions for producing the subunit, and isolating the subunit from the cell culture. The cell can be any cell expressing the subunit including a cell from a strain of *A. johnsonii* or a host cell containing a vector of this invention.

The present invention provides a composition containing a 1,3-dicarbonyl-dioxygenase. The enzyme can be mixed with buffers, salts, stabilizing agents, detergents and other components well known in the art to formulate products for the cleavage, decontamination or detoxification of acetylacetone and other 1,3-dicarbonyl compounds including cellular signaling substances based on homoserine lactones.

Finally, the present invention provides a method of cleaving a 1,3-dicarbonyl compound by reacting the compound with a 1,3-dicarbonyl-dioxygenase. The method can be used to decontaminate or detoxify 1,3-diketones, β-ketoamides, β-keto esters and 1,3-diesters.

The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

FIG. 4 presents the nucleotide sequence (SEQ ID NO: 1) and deduced amino-acid sequence (SEQ ID NO: 2) of the *A. johnsonii* 1,3-dicarbonyl-dioxygenase, and presents the nucleotide sequence of the *A. johnsonii* 1,3-dicarbonyl-dioxygenase gene and surrounding sequences (SEQ ID NO: 12)

DETAILED DESCRIPTION

Figure 1:
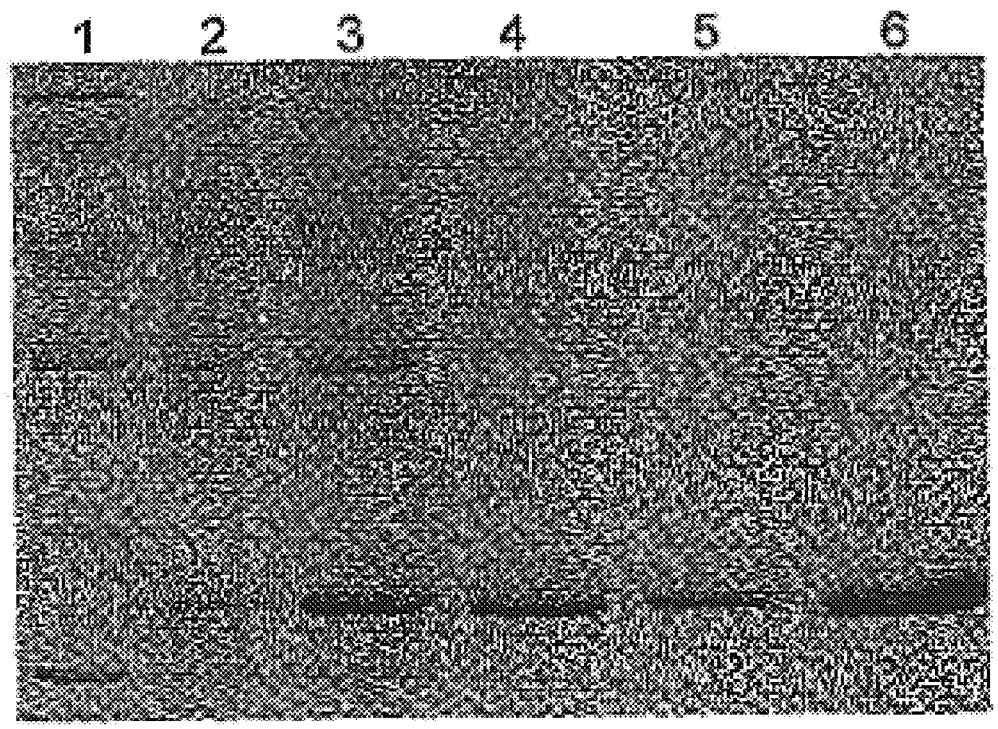
FIG. 1 is a picture of an SDS gel showing the purification of the *A. johnsonii* 1,3-dicarbonyl-dioxygenase.

The present invention relates to a newly isolated enzyme that cleaves 1,3-dicarbonyl compounds such as 1,3-diketones, β-ketoamides, β-keto esters and 1,3-diesters by incorporating molecular oxygen into the substrate in amounts equimolar to the amount of substrate cleaved. An enzyme that catalyzes such a cleavage under suitable reaction conditions is referred to herein as an enzyme exhibiting 1,3-dicarbonyl-dioxygenase activity. For convenience, an enzyme exhibiting 1,3-dicarbonyl-dioxygenase activity can be referred to as a 1,3-dicarbonyl-dioxygenase.

Suitable substrates for the enzyme can include 1,3-dicarbonyl compounds having the general structure

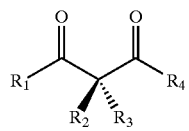

where $R_1$, and $R_4$ are independently selected from C1–C12 alkyl, alkoxyl, alkylamino and aryl groups, and $R_2$ and $R_3$ are independently selected from H and C1–C12 alkyl groups. Preferably, $R_1$, $R_2$, $R_3$, and $R_4$ alkyl groups are n-alkyl groups. Also, preferably, at least one of $R_2$ and $R_3$ is H. Additional substrates can have the general structure. Preferred substrates are acetylacetone, 1-phenyl-1,3-butanedione, 3-methylpentanedione, 5,5-dimethylhexane-2, 4-dione, 2,4-octanedione, 2,4-nonanedione, 2-acetocyclopentanone, 2-acetocyclohexanone, 3-oxobutanoic acid esters, 2-alkyl-3-oxobutanoic acid esters, 2-aryl-3-oxobutanoic acid esters, 2-aralkyl-3-oxobutanoic acid esters, and 2,4-dioxo-pentanoic-acid-ester and the like.

A 1,3-dicarbonyl-dioxygenase of this invention can be a monomeric enzyme made up of a single polypeptide, or a multimeric enzyme made up of two or more polypeptide subunits. For convenience, a single polypeptide of the multimeric enzyme can be referred to as a subunit of the enzyme.

In a preferred embodiment, the 1,3-dicarbonyl-dioxygenase of this invention has a molecular weight of about 67 kilodaltons under native conditions. Another preferred embodiment is a 1,3-dicarbonyl-dioxygenase made up of one or more subunits, each subunit having a molecular weight of about 16.6 kilodaltons.

A 1,3-dicarbonyl-dioxygenase of this invention can be a naturally occurring, recombinant or chemically synthesized enzyme. A naturally occurring enzyme is derived from a natural source, which can be a prokaryotic or eukaryotic cell that metabolizes acetylacetone, preferably a cell from a microorganism, more preferably a prokaryotic cell, even more preferably a cell from a strain of the family Moraxellaceae, which according to the National Center for Biotechnology Information taxonomy database (publicly accessible on the World Wide Web at ncbi.nim.nih.gov) includes the genera Acinetobacter, Moraxella and Psychrobacter, more preferably still a cell from a strain of Acinetobacter, Moraxella or Psychrobacter, most preferably a cell from a strain of *A. johnsonii*.

A recombinant 1,3-dicarbonyl-dioxygenase is derived from host cells containing a vector of this invention. Recombinant proteins derived from host cells often contain modifications not present in the naturally occurring protein. Proteins can be modified by glycosylation, acetylation, phosphorylation, lipidation and other modifications well known in the art. Such modified 1,3-dicarbonyl-dioxygenases are encompassed by the present invention.

An enzyme within the scope of this invention can be an altered form of a 1,3-dicarbonyl-dioxygenase. As used herein, the term "altered form" refers to a protein that has been treated to change its naturally occurring structure. Altered It forms of a 1,3-dicarbonyl-dioxygenase may better perform a decontamination or detoxifying role. An altered form can be prepared, for example, by covalent modification of a 1,3-dicarbonyl-dioxygenase, by crosslinking a 1,3-dicarbonyl-dioxygenase to an insoluble support matrix, by crosslinking a 1,3-dicarbonyl-dioxygenase to a second protein, or by obtaining an enzymatically active fragment of a 1,3-dicarbonyl-dioxygenase.

Covalent modifications can be introduced into an enzyme by reacting targeted amino acid residues of the purified or crude enzyme with an organic derivatizing agent that is capable of reacting with selected side chains or terminal residues. Covalent modification of proteins using organic derivatizing agents is well known to those of skill in the art. For example, cysteinyl residues can be reacted with α-haloacetates (and corresponding amines), such as chloroacetic acid or chloroacetamide, to give carboxymethyl or carboxyamidomethyl derivatives. Histidyl residues can be derivatized by reaction with diethylpyrocarbonate at pH 5.5–7.0, or with para-bromophenacyl bromide at pH 6 in 1 M sodium cacodylate. Lysinyl and amino terminal residues can be reacted with succinic or other carboxylic acid anhydrides. Arginyl residues can be modified by reaction with one or several conventional reagents, among them phenylglyoxal, 2,3-butanedione, 1,2-cyclohexanedione, and ninhydrin. Spectral labels can be introduced into tyrosyl residues by reaction with aromatic diazonium compounds or tetranitromethane; most commonly, N-acetylimidizol and tetranitromethane are used to form 0-acetyl tyrosyl species and 3-nitro derivatives, respectively. Carboxyl side groups (aspartyl or glutamyl) can be selectively modified by reaction with carbodiimides (R'—N—C—N—R') such as 1-cyclohexyl-3-(2-morpholinyl-(4-ethyl) carbodiimide or 1-ethyl-3 (4 azonia 4,4-dimethylpentyl) carbodiimide. Furthermore, aspartyl and glutamyl residues are converted to asparaginyl and glutaminyl residues by reaction with ammonium ions. Glutaminyl and asparaginyl residues can be deamidated to the corresponding glutamyl and aspartyl residues. Other modifications include hydroxylation of proline and lysine, phosphorylation of hydroxyl groups of seryl or threonyl residues, methylation of the α-amino groups of lysine, arginine, and histidine side chains (T. E. Creighton, 1983, Proteins: Structure and Molecule Properties, W. H. Freeman & Co., San Francisco, pp. 79–86), acetylation of the N-terminal amine, and, in some instances, amidation of the C-terminal carboxyl groups.

Crosslinking of a 1,3-dicarbonyl-dioxygenase to a water-insoluble support matrix can be performed with bifunctional agents well known in the art including 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), and bifunctional maleimides such as bis-N-maleimido-1,8-octane. Bifunctional agents such as methyl-3-[(p-azidophenyl)dithio]propioimidate yield photoactivatable intermediates that are capable of forming crosslinks in the presence of light. Alternatively, reactive water-insoluble matrices such as cyanogen bromide-activated carbohydrates can be employed for protein immobilization.

Crosslinking of a 1,3-dicarbonyl-dioxygenase to a second protein, including a second 1,3-dicarbonyl-dioxygenase, can be performed using the bifunctional reagents described herein.

Obtaining an enzymatically active fragment of a 1,3-dicarbonyl-dioxygenase an be performed by methods well known to those of skill in the art. As used herein, the term "fragment" refers to a portion of a 1,3-dicarbonyl-dioxygenase. A fragment can be produced, for example, by partially digesting a 1,3-dicarbonyl-dioxygenase with a protease, for example trypsin, and purifying the digestion products that retain 1,3-dicarbonyl-dioxygenase activity. Alternatively, a polynucleotide encoding a portion of a 1,3-dicarbonyl-dioxygenase subunit can be expressed in a heterologous expression system and expressed products having 1,3-dicarbonyl-dioxygenase activity can be purified.

An enzyme within the scope of this invention can be a 1,3-dicarbonyl-dioxygenase that is antigenically related to *A. johnsonii* 1,3-dicarbonyl-dioxygenase. Two proteins which are antigenically related display immunological cross-reactivity. For example, antibodies to the first protein also recognize the second protein.

Antibodies to *A. johnsonii* 1,3-dicarbonyl-dioxygenase can be prepared by methods that are well known in the art (see, e.g., Antibodies: A Laboratory Manual, Cold Spring Harbor Laboratory, 1988). A wide range of animal species can be used for the production of antibodies. Typically the animal used for production of antibodies is a rabbit, a mouse, a rat, a hamster, a guinea pig and/or a goat. Antiserum can be used as is for various applications. Alternatively, the desired antibody fraction can be purified by well-known methods such as affinity chromatography using another antibody, protein A and protein G chromatography, and chromatography using a peptide bound to a solid matrix.

Immunological cross-reactivity can be determined using standard immunological assays well known in the art. For example enzyme linked immunosorbent assay (ELISA) can be performed by immobilizing a 1,3-dicarbonyl-dioxygenase onto the well surface of a microtiter plate, then contacting the immobilized 1,3-dicarbonyl-dioxygenase with antibodies to *A. johnsonii* 1,3-dicarbonyl-dioxygenase. After washing to remove unbound and non-specifically bound antibody, the bound antibody can be detected. Where the initial antibodies are linked to a detectable label, the bound antibody can be detected directly. Alternatively, the bound antibody can be detected using a second antibody that has binding affinity for the first antibody, with the second antibody being linked to a detectable label.

The present invention provides an isolated 1,3-dicarbonyl-dioxygenase containing one or more subunits, each subunit comprising the amino acid sequence set forth in SEQ ID NO: 2. Also included within the scope of this invention is an isolated enzyme containing one or more subunits, each subunit comprising an amino acid sequence that is at least 70% identical to SEQ ID NO: 2, preferably at least 80% identical, more preferably at least 90% identical, most preferably at least 95% identical, as determined by BLAST analysis.

To compare a nucleotide or polypeptide sequence with the corresponding SEQ ID NO: 1 or SEQ ID NO: 2 sequence, a global alignment of the sequences can be performed using the BLAST programs publicly available through the National Center for Biotechnology Information (on the World Wide Web at ncbi.nlm.nih.gov). Prior to performing a global alignment, SEQ ID NO: 1 or SEQ ID NO: 2 can be submitted to GenBank. Default parameters provided by the National Center for Biotechnology Information can be used for a global alignment.

The present invention provides an isolated polypeptide subunit of a 1,3-dicarbonyl-dioxygenase. A subunit is considered within the scope of this invention if it is biologically active. The term "biologically active subunit" refers to a subunit that is capable of forming a 1,3-dicarbonyl-dioxygenase. A biologically active subunit can be, for example, a subunit isolated from a purified 1,3-dicarbonyl-dioxygenase, a recombinant subunit that is identical to a subunit isolated from a purified 1,3-dicarbonyl-dioxygenase, or a subunit shown empirically to form a 1,3-dicarbonyl-dioxygenase.

In a preferred embodiment, the isolated subunit has a molecular weight of about 16.6 kilodaltons, In another preferred embodiment, the isolated subunit is derived from a 1,3-dicarbonyl-dioxygenase having a molecular weight of about 67 kilodaltons under native conditions.

A subunit of this invention can be a native, recombinant or chemically synthesized subunit. Native and recombinant subunits can be derived from the same sources described herein for native and recombinant enzymes, respectively. Recombinant subunits can be modified by host cells as described herein for recombinant enzymes. A subunit within the scope of this invention can be an altered form of a 1,3-dicarbonyl-dioxygenase subunit. Altered forms of subunits can be prepared as described herein for altered forms of 1,3-dicarbonyl-dioxygenase. A subunit that is antigenically related to an *A. johnsonii* 1,3-dicarbonyl-dioxygenase subunit is also encompassed by this invention.

The present invention provides an isolated polypeptide subunit comprising the amino acid sequence set forth in SEQ ID NO: 2. Also included within the scope of this invention is an isolated, biologically active subunit comprising an amino acid sequence that is at least 70% identical to SEQ ID NO: 2, preferably at least 80% identical, more preferably at least 90% identical, most preferably at least 95% identical, as determined by BLAST analysis.

In accordance with this invention, a subunit having an amino acid sequence that differs from SEQ ID NO: 2 can be naturally occurring or artificially designed. A subunit with conservative amino acid substitutions can be designed by replacing an amino acid residue of SEQ ID NO: 2 with a chemically similar amino acid in accordance with the substitutions presented in Table 1.

TABLE 1

CHEMICALLY SIMILAR RESIDUES

| Original Residue | Substitution |
| --- | --- |
| ala | gly; ser |
| arg | lys |
| asn | gln; his |
| asp | glu |
| cys | ser |
| gln | asn |
| glu | asp |
| gly | ala; pro |
| his | asn; gln |
| ile | leu; val |
| leu | ile; val |
| lys | arg; gln; glu |
| met | leu; tyr; ile |
| phe | met; leu; tyr |
| ser | thr |
| thr | ser |
| trp | tyr |
| tyr | trp; phe |
| val | ile; leu |

To design more divergent subunits, deletions or insertions of amino acids residues can be included.

An artificially designed subunit can be obtained by site-specific mutagenesis of DNA using methods well known in the art. For example, a primer spanning a mutation site can be annealed to a polynucleotide containing SEQ ID NO: 2 cloned in the single-stranded phage vector M13. The primer can be extended by a DNA polymerase such as *E. coli* DNA polymerase Kienow fragment. The resulting heteroduplex DNA can be transformed into appropriate bacterial cells such as JM101, and clones containing the mutation can be isolated. The mutated polynucleotide can be inserted into an expression vector and the resulting subunit can be expressed in a suitable host cell.

A subunit within the scope of this invention can be a fusion protein containing a 1,3-dicarbonyl-dioxygenase subunit attached to a heterologous protein. A heterologous protein has an amino acid sequence not substantially similar to the 1,3-dicarbonyl-dioxygenase subunit. The heterologous protein can be fused to the N-terminus or C-terminus of the 1,3-dicarbonyl-dioxygenase subunit. Fusion proteins can include, but are not limited to, enzymatic fusion proteins, for example beta-galactosidase fusions, poly-His fusions, MYC-tagged fusions and Ig fusions. Such fusions proteins, particularly poly-His fusions, can facilitate the purification of recombinant 1,3-dicarbonyl-dioxygenase subunits.

A fusion protein can be produced by standard recombinant DNA techniques. For example, PCR amplification of gene fragments can be carried out using anchor primers which give rise to complementary overhangs between two consecutive gene fragments. The fragments can be annealed and re-amplified to generate a chimeric gene sequence (Ausubel et al., Current Protocols in Molecular Biology, 1992). The chimeric gene can be expressed in an appropriate host cell. Alternatively, a DNA fragment encoding a 1,3-dicarbonyl-dioxygenase subunit can be cloned in a commercially available expression vector that already contains a heterologous protein, with the result being a 1,3-dicarbonyl-dioxygenase fused in-frame to the heterologus protein.

The present invention provides an isolated polynucleotide encoding a biologically active 1,3-dicarbonyl-dioxygenase subunit in which the polynucleotide comprises the nucleotide sequence set forth in SEQ ID NO: 1. Also provided is an isolated polynucleotide encoding a biologically active 1,3-dicarbonyl-dioxygenase subunit in which the polynucleotide comprises a nucleotide sequence that is at least 60% identical to SEQ ID NO: 1, preferably at least 70% identical, more preferably at least 80% identical, even more preferably at least 90% identical, most preferably at least 95% identical, as determined by BLAST analysis.

The present invention also provides a polynucleotide encoding a biologically active 1,3-dicarbonyl-dioxygenase subunit in which the polynucleotide comprises the nucleotide sequence set forth in SEQ ID NOs: 3, 4, 8, 9, 10 or 11.

In accordance with this invention, a polynucleotide having a nucleotide sequence that differs from SEQ ID NO: 1 can be naturally occurring or artificially designed. Artificially designed polynucleotides can be produced using the site-specific mutagenesis methods described herein.

The present invention provides a vector containing a nucleotide sequence described herein. The vector can be a cloning vector for maintaining nucleic acid molecules, or an expression vector. A variety of cloning and expression vectors are well known to those of skill in the art. Examples include plasmid vectors, single or double stranded phage vectors, single or double stranded DNA or RNA viral vectors, or artificial chromosomes, such as BAC and YAC. An expression vector contains a nucleotide sequence described herein operably linked to a promoter. Promoters, terminators and other regulatory regions suitable for controlling transcription and translation in a variety of prokaryotic and eukaryotic host cells are well known in the art (Sambrook et al., Molecular Cloning: A Laboratory Manual. 2nd ed., Cold Spring Harbor Laboratory Press, Cold Spring Harbor, N.Y., 1989).

The invention further provides a host cell containing an expression vector of this invention. The host cell can be a mammalian cell, plant cell, insect cell, yeast and other fungi, or bacteria. Suitable host cells for various expression vectors are well known to those of skill in the art (Sambrook et al., Molecular Cloning: A Laboratory Manual. 2nd ed., Cold Spring Harbor Laboratory Press, Cold Spring Harbor, N.Y., 1989).

An expression vector can be introduced into a suitable host cell by techniques such as calcium phosphate transfection, DEAE-dextran-mediated transfection, cationic lipid-mediated transfection, electroporation, transduction, infection, lipofection, and other techniques well known to those in the art (Sambrook, et al. Molecular Cloning: A Laboratory Manual. 2nd, ed., Cold Spring Harbor Laboratory, Cold Spring Harbor Laboratory Press, Cold Spring Harbor, N.Y., 1989).

The present invention provides a process for producing a 1,3-dicarbonyl-dioxygenase comprising the steps of (a) culturing a cell expressing the enzyme under conditions sufficient to produce the enzyme, and (b) isolating the enzyme from the cell culture. The cell can be a naturally occurring cell from a prokaryote or eukaryote, preferably a cell from a microorganism, more preferably from a prokaryote, even more preferably from a strain of the family Moraxellaceae, more preferably still from a strain of Acinetobacter, Moraxella or Psychrobacter, most preferably from a strain of *A. johnsonii*. The cell can also be a host cell containing an expression vector of this invention.

The present invention also provides a process for producing a 1,3-dicarbonyl-dioxygenase subunit comprising the steps of (a) culturing a cell expressing the subunit under conditions sufficient to produce the subunit, and (b) isolating the subunit from the cell culture. The cell can be a naturally occurring cell from a prokaryote or eukaryote, preferably a cell from a microorganism, more preferably from a prokaryote, even more preferably from a strain of the family Moraxellaceae, more preferably still from a strain of Acinetobacter, Moraxella or Psychrobacter, most preferably from a strain of *A. johnsonii*. The cell can also be a host cell containing an expression vector of this invention.

The present invention provides a composition comprising a 1,3-dicarbonyl-dioxygenase of this invention. Depending on the intended use, the composition can be mixed with one or more additional components, for example, a buffer such as $KH_2PO_4$ or tris-acetate, preferably at a pH of about 6 to about 7.5, a salt such as NaCl, a stabilizing agent such as glycerol, a detergent such as Tween-20, and other components well known in the art. Such mixtures provide a means to cleave, decontaminate and detoxify acetylacetone and other 1,3-dicarbonyl compounds.

Finally, the present invention provides a method of cleaving a 1,3-dicarbonyl compound such as a 1,3-diketone, β-ketoamides, β-keto ester or 1,3-diester, the method comprising reacting the compound with a 1,3-dicarbonyl-dioxygenase in the presence of molecular oxygen. Cleavage of acetylacetone by this method gives rise to equimolar amounts of acetate and methylglyoxal. A diketone of this method can have the general structure.

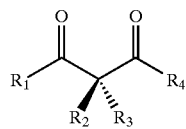

where $R_1$ is selected from C2–C12 alkyl groups and C1–C12 alkoxyl and aryl groups, $R_2$ and $R_3$ are independently selected from H and C1–C12 alkyl groups, and $R_4$ is selected from C1–C12 alkyl, alkoxyl, and aryl groups. Preferably, $R_1$, $R_2$, $R_3$, and $R_4$ alkyl groups are n-alkyl groups. Also, preferably, at least one of $R_2$ and $R_3$ is H. Preferred substrates are 1-phenyl-1,3-butanedione, 3-methylpentanedione, 5,5-dimethylhexane-2,4-dione, 2,4-octanedione, 2,4-nonanedione, 2-acetocyclopentanone, 2-acetocyclohexanone, 3-oxobutanoic acid esters, 2-alkyl-3-oxobutanoic acid esters, 2-aryl-3-oxobutanoic acid esters, 2-aralkyl-3-oxobutanoic acid esters, and 2,4-dioxo-pentanoic-acid-ethyl-ester.

EXAMPLES

The present invention may be better understood by referring to the accompanying examples, which are intended for illustration purposes only and should not in any sense be construed as limiting the scope of the invention as defined in the claims appended hereto.

Example 1

Procedures

Strain and Media

A strain was isolated from slurry by growth on acetylacetone as sole carbon-source in a minimal-medium (M9). It was identified as *A. johnsonii* (DSM ID 98-849). The strain was kept on Lenox-broth-plates at 30° C. For enzyme-production of the wild type Acinetobacter strain an optimized fermentation medium and procedure (Mandl et. al., Biotechnology 2000, DECHEMA Annual Meeting on Biotechnology, Berlin, Germany, 3–8 September 2000) were applied. The full medium, supplied with 1.6 g/L of acetylacetone was inoculated with an over-night culture of *A. johnsonii* to an OD of 1 and incubated at 30° C. on rotatory shakers in erlenmeyer flasks. After 6 hours further acetylacetone (1 g/L) was added to the medium. Incubation was continued for another three hours, then the cells were harvested.

Expression constructs were expressed in *E.coli* XL1 Blue (Stratagene, La Jolla, Calif.), which was grown to an OD of 1 at 30° C. on rotatory shakers in erlenmeyer flasks, then induced with IPTG (0.3 mM) and incubated for another 5 hours.

Cells were harvested by centrifugation, resuspended in two volumes of phospate buffer (50 mM, pH 7.5) and stored at −20° C.

Purification of the Enzyme

Purification of 1,3-dicarbonyl-dioxygenase was performed at 4° C. by using a fast performance liquid chromatography system (Amersham Pharmacia Biotech, Piscataway, N.J.).

Cells were disrupted by sonication. The lysate was centrifuged at 100,000 g for one hour. The resulting soluble fraction was submitted to purification.

Fast-Flow-Anion-Exchange-Chromatography

The cell-lysate (100000 g-fraction) containing 700–900 mg protein was applied to a QFF-Sepharose™ column (25 mL, Pharmacia). Unbound material was eluted by Tris/HCl-buffer, pH 7.5, 20 mM. This procedure was followed by application of a NaCl-gradient (0–0.17M NaCl). After rinsing the column with one column volume of buffer, to detach further protein, the 1,3-dicarbonyl-dioxygenase eluted with buffer of a salt concentration of 0.22M NaCl.

Hydrophobic-Interaction-Chromatography

Active fractions from (1) were pooled and concentrated 2-3 fold (Millipore Biomax™ 15 mL concentration devices, Millipore Corporation, Bedford, Mass.). Ionic strength was adjusted by adding NaCl to a final concentration of 4M NaCl. The protein-solution was applied to a Phenyl-Sepharose™ column (20 mL, Pharmacia). Unbound protein was eluted with $KH_2PO_4$-buffer, 50 mM, pH 7.5. Applying a stepwise gradient 1,3-dicarbonyl-dioxygenase was eluted with 1.2 M NaCl.

Gel-Filtration

The active fractions from (2) were pooled and concentrated to 200–500 µL end-volume. Per run 500 µL of the concentrate was applied to a Superdex™ 200 gel-filtration column and eluted with Tris/acetic acid buffer, 5 mM, pH 7.5 or $KH_2PO_4$-buffer, 50 mM, pH 7.5.

Anion-Exchange Chromatography

As final purification step the active fractions from gel filtration were applied to the high resolution anion-exchange column RESOURCE™ Q (6 mL, Pharmacia). The elution-conditions of the first purification step (1) were applied.

Polyacrylamide Gel Electrophoresis

SDS-PAGE was done in 12% gel by the method of Laemmli. To reduce disulfide-bonds, proteins were incubated with mercaptoethanol at 95° C. for 5 minutes. Protein was stained with Coomassie brilliant blue R-250, and destained with 10% acetic acid in 30% methanol.

Determination of the Molecular Weight of the Protein

The molecular weight of the denaturated enzyme was determined by SDS-PAGE (12.5% acrylamide) using molecular weight protein markers (Bio-Rad SDS-PAGE standard low mol. Weight, Bio-Rad Laboratories, Hercules, Calif.). The size of the native enzyme was determined by gel-filtration with a 16/10 Superdex Determination of the pI Isoelectric focussing was done with the Ready Gel™ system of Bio-Rad. Protein was stained with Coomassie blue R250 and crocein scarlet (0.05%). An isoelectric focussing calibration kit (pI 4.45–9.6) from Bio-Rad was used for calibration.

UV Activity-Assay for Acetyl-Acetone-Cleaving Enzyme

The enzyme-activity was determined UV-spectrophotometrically (Spectronic Genesis 2PC, Thermo Spectronic, Rochester N.Y.) by measuring the decrease of acetyl-acetone at 280 nm (at pH 7.5, $\epsilon$ was determined to be 2240 [L/(M*cm)]). The standard conditions for the activity-assay were oxygen-saturated $KH_2PO_4$-buffer, 50 mM, pH 7.5, acetyl-acetone 0.25 mM, 5–100 $\mu$L of enzyme in a total volume of 1 mL. The reaction rates were determined by using the microcomputer regression program provided with the spectrophotometer (Winspec) based on the first ten absorbance measurements made at 5-s intervals. One unit of enzyme-activity was defined as 1 $\mu$mol of acetyl-acetone cleaved per minute.

Determination of the Molar Absorbance Coefficient for Various Substrates

Substrates were dissolved at a concentration of 0.001–1 mM in $KH_2PO_4$-buffer, 50 mM, pH 7.5 using a 10 mM stock solution. Duplicate absorption-measurements of 20 different dilutions were performed at 25° C. The molar absorption coefficients were calculated by linear regression.

Oxygen-Consumption-Rate-Measurements

Oxygen consumption during the enzyme reaction was measured with an oxygen-electrode-cell (Digital Oxygen System Model 10, Rank Brothers Ltd., Cambridge, England) as described previously (Beechey, R. B. and Ribbons, D. W. (1971). 'Methods in Microbiology'.V. 6B. Edited by J. R. Norris and D. W. Ribbons. Academic press, London. 'Oxygen electrode measurements' (Chapter II) pp. 29–52.). The reaction mixture contained air-saturated $KH_2PO_4$-buffer, 50 mM, pH 7.5 at 25° C. (thermostat). The oxygen-electrode was calibrated by the sodium-sulfite-method. Varying concentrations of substrate (0.01–0.3 mM) were added and the resulting decrease of oxygen was determined.

Analysis of Enzyme Kinetics

The apparent $K_s$ and $V_{max}$-values were determined by photometric measurements in oxygen-saturated buffer with substrate concentrations of to 10–200 $\mu$M. Under these conditions, oxygen limitation was avoided and no effect of substrate inhibition was observed. Assuming the Michaelis-Menten-equation, $V_{max}$ and $K_s$ values were calculated by non-linear curve-fit by the program microcal-origin. $K_{O2}$ was estimated by polarographic methods, adding non limiting amounts of substrate (0.5–1 mM) and graphically determining the oxygen concentration at the point of half of the maximum activity. $K_s$-values were similarly confirmed by polarographic methods, by stepwise addition of substrate to a final concentration of 20–150 $\mu$M.

Determination of Enzyme-Activity and Stability

Activity measurements were performed with the oxygen-electrode, with $KH_2PO_4$-buffers adjusted to various pH-values [5.0–9.0]. For stability measurements, the enzyme was diluted ten-fold and incubated at various pH-values [5.0–9.0]. The activity was measured periodically with the UV-activity-assay.

Protein Determinations

Protein content was determined by the BCA-Method (Pierce, Rockford, Ill.). Calibration was performed by measuring BSA-standard solutions simultaneously.

Substrates

The substrates were purchased from Aldrich (Sigma-Aldrich, St. Louis, Mo.), apart from nonanedione octanedione and 5,5-dimethylhexanedione, which were products from Lancaster (Lancaster Synthesis, Lancashire, England). All these commercial starting materials were used without purification. Acetopyruvate (2,4-diketopentanoate) (Brecker, L., M. Pogorevc, H. Griengl, W. Steiner, T. Kappe, and D. W. Ribbons. 1998. Synthesis of 2,4-diketoacids and their aqueous solution structures. New J. Chem. 23: 437–446.), ethyl-acetopyruvate (ethyl-2,4-diketopentanoate) (Brecker et al., supra), 4-methoxy-pent-3-en-2-one (Stork, G. and G. A. Kraus. 1976. A new Synthesis of Vinylogous Aldols and Polyenones. J. Am. Chem. Soc. 98: 2351–2352.) and 3,3-dimethylacetoacetone (Mao, C.-L., F. C. Frostick Jr., E. H. Man, R. M. Manyik, R. L. Wells and C. R. Hauser. 1969. Dual Formation of β Diketones from Methylene Ketones and Acetic Anhydride by Means of Boron Trifluoride. Improved Method of Synthesis of Certain β Diketones. J. Org. Chem. 34: 1425–1429.) were synthesized as described elsewhere.

Reaction Analysis

The products of the enzyme reaction were identified directly from the reaction mixture by in situ $^1$H-NMR-spectroscopy (Pokorny, D., L. Brecker, M. Pogorevc, H. Griengl, W. Steiner, T. Kappe, and D. W. Ribbons. 1999. Proton-Nuclear Magnetic Resonance Analyses of the Substrate Specificity of a β-Ketolase from *Pseudomonas putida*, Acetopyruvate Hydrolase. J. Bacteriol. 181: 5051–5059.). Therefore a 200 MHz narrow bore magnet (Varian Gemini™ 2000, Varian, Inc., Palo Alto, Calif.) and a 5 mm broadband probe head were used. The NMR tube was rotated at 20 rps. For a lock a $D_2O$ vortex capillary was added to avoid $^1$H/D exchange reactions. The overwhelming water-signal was suppressed with a presaturation method (Guéron, M., P. Plateau and M. Decorps. 1991. Solvent signal suppression in NMR. Prog. NMR Spectrosc. 23: 135–209. Hore, J. P. 1989. Solvent suppression. p. 64. In N. J. Oppenheimer and J. T. James (eds.), Methods Enzymol. 176. Academic Press, Inc., San Diego.). The following parameters were adjusted for a $^1$H-frequency of 200 MHz: presaturation-duration of 1.0 s, $^1$H-pulse-angle of 90, an acquisition-time of 2.0 s and a relaxation delay of 1.5 s. 64 Scans were accumulated and after a zero filling to 32 k datapoints the free induction decay was Fourier transformed. The water signal (4.70 ppm) was used as a reference. For standard reaction analytics HPLC-measurements were performed (Hewlett-Packard, column: Aminex-HPX-87H, UV- and RI-detector, eluent Sulfuric acid 0.005 M).

Inhibition Studies

The freshly prepared solutions of the respecitive inhibitors in buffer were added to partially purified enzyme, which then was incubated at room temperature. Activity was measured by the oxygen electrode assay as described previously (25° C., 0.5 mM acetylacetone end-concentration in the mixture).

Protein Sequencing

The protein band from a highly purified enzyme preparation was cut out from an SDS-gel and sent to Protana (MDS Proteomics, Odense, Denmark) for sequencing. The purified protein was tryptically digested and the resulting peptides were separated by HPLC. The sequence of the peptides was determined by stepwise detachment of the amino acids and determining the molecular weight of the remaining peptide by Maldi-Tof.

Isolation of DNA and PCR-Reaction with Degenerate Oligonucleotides

Vector DNA was isolated using the Wizard® Plus SV Minipreps-kit (Promega Corporation, Madison, Wis.). Total DNA from A. johnsonii was isolated with QIAGEN® Genomic-tips (Qiagen, Hilden, Germany) according to the QIAGEN Genomic DNA Purification Procedure. Degenerate oligonucleotides "a" and "b" (see SEQ ID NOs. 8 and 9 below) were synthesized at the Institute of Biotechnology, TU-Graz. Amplification was performed with 1 U of HotStarTaq-polymerase (Qiagen), 200 pmol of primers, 100 $\mu$M of each desoxynucleoside triphosphate and 100 ng of DNA with an annealing temperature of 50° C. for the first 5 cycles and 55° C. for further 25 cycles. Resulting PCR-products were directly cloned with the TOPO™ TA-cloning® kit (Invitrogen, Carlsbad, Calif.) and sequenced.

Southern Blot

According to the standard procedure from a Boehringer-Dig-labelling-kit (Roche Molecular Biochemicals, Indianapolis, Ind.), a Dig-labeled PCR-product was synthesized with degenerate oligonucleotides "a" and "b" (see SEQ ID NOs. 8 and 9 below) as primers and with A. johnsonii chromosomal DNA as a template. A Southern blot was performed at 65° C. with chromosomal DNA previously digested with EcoRI, SacI and HindIII respectively and with the labeled PCR-product by a standard procedure (Boehringer Mannheim GmbH, Mannheim, The DIG System User's guide for Filter Hybridization, 1993)).

Construction of a DNA-Library

Total DNA from A. johnsonii was digested with EcoRI and purified in a 0.8% agarose-gel. Fragments of 2–4 kb in size were eluted with a QIAquick® Gel Extraction Kit (QIAGEN) and ligated with a vector pBluescript II SK (−) (Stragagene), which had previously been digested with EcoRI and dephosphorylated. The recombinant plasmids were transformed into competent E.coli XL1 Blue cells by standard procedures (Sambrook, J. et al., Molecular Cloning: A Laboratory Manual. 2nd ed., Cold Spring Harbor Laboratory Press, Cold Spring Harbor, N.Y., 1989), harvested and the gene-library-vector-DNA was isolated. PCR reactions with the resulting vector-DNA as a template; the vector specific primers T7 and T3 and the gene-specific primers 2405 and 2406 (see SEQ ID NOs. 10 and 11 below) were performed at 57° C. The resulting PCR-products were sequenced.

Over-Expression of the 1,3-dicarbonyl-dioxygenase-gene in pMS470

The gene of the 1,3-dicarbonyl-dioxygenase was amplified from A. johnsonii genomic DNA by using Pwo DNA Polymerase (Roche Molecular Biochemicals, Indianapolis, Ind.). Appropriate primers were designed based on the sequence information gained from the PCR-products which had been amplified from the gene-library. The forward primer was engineered with an NdeI-site:

5'-CTATA CATATGGATTATTGTAATMAAAACACACTG-3' (SEQ ID NO: 3)

which overlapped the initiation codon of each gene. The reverse primer, complementary to a convenient sequence downstream of the respective ORF, was engineered with a HindIII site:

5'-GACAAGCTTCGGATTTCCTCCMTCCACG-3' (SEQ ID NO: 4)

(underlined regions indicate engineered restriction sites). Amplification was performed with 1 U of pwo-polymerase, which has proof-reading-activity, 200 $\mu$M of primers, 100 $\mu$M of each desoxynucleoside triphosphate and 100 ng of DNA at 62° C. (30 cycles). The amplified, NdeI and HindIII-restricted gene was purified in a 0.8% agarose gel by elution with a QIAEX® kit (QIAGEN) and cloned behind the strong inducible tac promotor, by cloning into the NdeI and HindIII sites of the expression plasmid pMS470 (see Balzer D, Ziegelin G, Pansegrau W, Kruft V, Lanka E. 1992. Nucleic Acids Res 20(8):1851–1858; and Petersen, Schwab. 2001. J. Biotechnol. 89:11–25). The resulting plasmid was sequenced again, to ensure that no mutations had been introduced into the sequence by PCR.

Example 2

Protein Purification from A. johnsonii

A. johnsonii 1,3-dicarbonyl-dioxygenase was purified using a four step chromatographic method. A typical set of data is shown in Table2.

TABLE 2

PURIFICATION OF WILD-TYPE PROTEIN

| Purification-step | Volume mL | Protein mg | Enzyme Total U | U/mg $\mu$M/min*mg | Protein mg/mL | Recovery % | Purification fold |
|---|---|---|---|---|---|---|---|
| cell-extract | 24.00 | 1008 | 642 | 0.6 | 42.0 | 100 | 1.0 |
| QFF | 50.00 | 230 | 669 | 2.9 | 4.6 | 104 | 4.6 |
| QFF-concentrate | 20.00 | 256 | 625 | 2.4 | 12.8 | 97 | 3.8 |
| Phenyl-sepharose | 15.00 | 24 | 241 | 10.0 | 1.6 | 38 | 15.8 |
| Ph.-seph.-conc. | 0.21 | 25.2 | 169 | 6.7 | 120.0 | 26 | 10.5 |
| Gel-filtration | 3.00 | 13.5 | 134 | 9.9 | 4.5 | 21 | 15.6 |
| ResourceQ | 12.00 | 11.5 | 108 | 9.4 | 1.0 | 17 | 14.7 |

The protein was purified to apparent homogeneity. The purity was confirmed by SDS-polyacrylamide gel-electrophoresis (FIG. 1). Referring to FIG. 1: lane 1 contains a molecular-weight-standard; lane 2 contains cell-extract (40 $\mu$g); lane 3 contains the active fraction after the QFF-column (50 $\mu$g); lane 4 contains the active fraction after the Phenyl Sepharose column (20 $\mu$g); lane 5 contains the active fraction after gel-filtration (5 $\mu$g); and lane 6: contains purified protein (25 $\mu$g). Enzyme purity was further investigated by non-denaturing and denaturing gel-electrophoresis on 8,12, 15 and 20% polyacrylamide gels. In each case a single stained protein band was obtained. The protein was stained by Commassie blue.

Example 3
Molecular Weight and Subunit Structure

Figure 2:
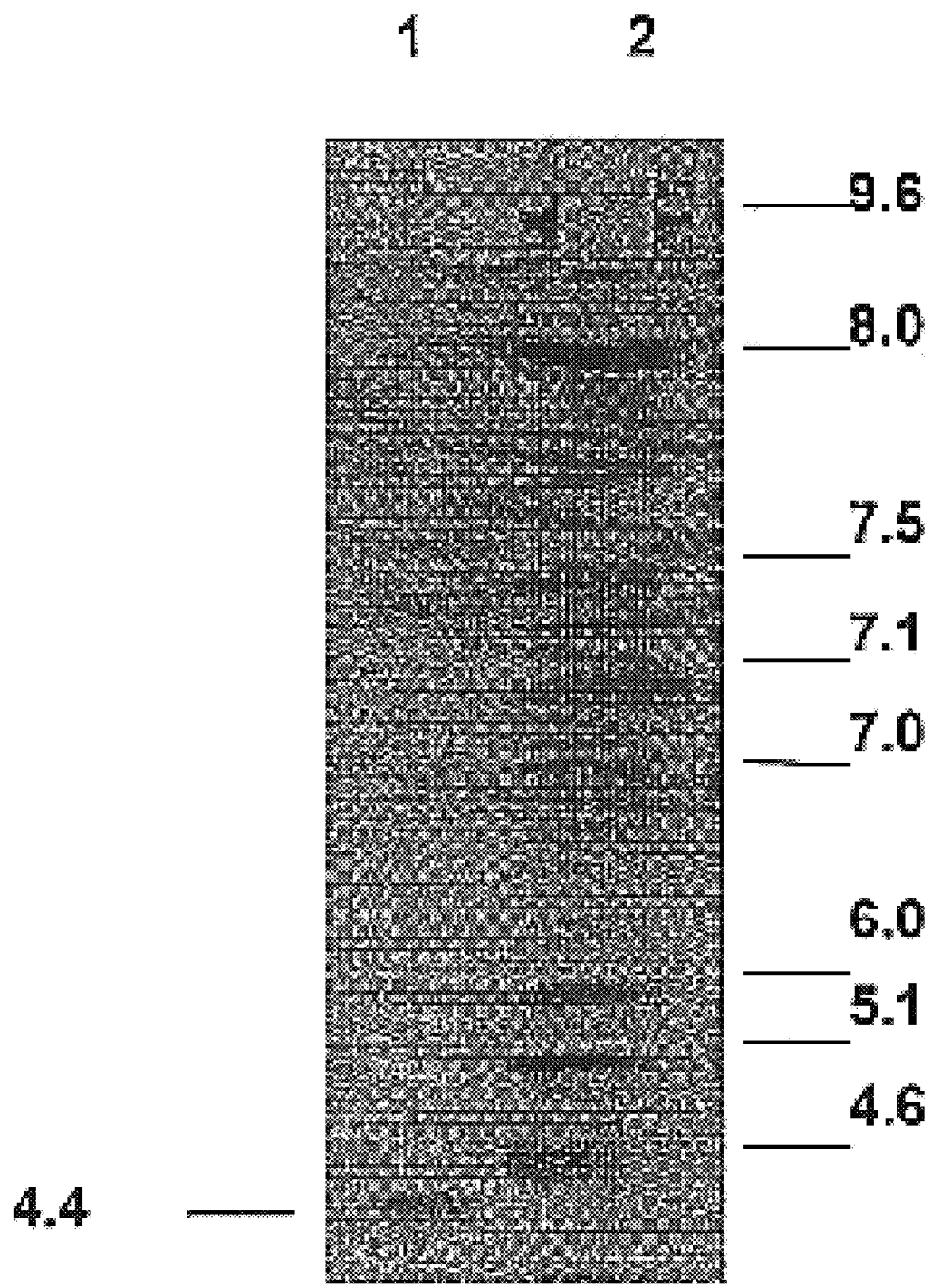
FIG. 2 is a picture of an IEF-gel showing the pI of the purified *A. johnsonii* 1,3-dicarbonyl-dioxygenase.

A molecular weight of 16.6 kDa was found by SDS-gel-electrophoresis under reducing as well as under non-reducing conditions (FIG. 1). The determination of the protein size by gel filtration under native conditions gave about 67 kDa (salt-concentration of the eluent:0 and 0.1 M NaCl). Isoelectric focussing of the purified protein gave a single band at pH 4.4 (FIG. 2, lane 1) in comparison with IEF standard proteins (FIG. 2, lane 2). These results suggest that the protein consists of four identical subunits of 16.6 kDa, which are not bound covalently.

Example 4
Reaction and Substrate Specificity

Using the unpurified cell-extract as catalyst for the degradation of acetyl-acetone, several products, such as newly formed acetate, pyruvate and lactate were detected by HPLC as well as by $^1$H-NMR (data not shown). The first step of acetyl-acetone degradation with crude cell extract, however, remained unclear. Repeating the experiment with the purified enzyme, without addition of any cofactor, one mmol of acetate (1H δ: 1.76 s) was found per mmol of acetyl-acetone (1 H δ: 2.11 s, 1.90 s) cleaved. Two further signals appeared concomitantly (1H δ: 2.14 s, 1.28 s). By polarographic methods the consumption of molecular oxygen was determined to be equimolar to the amount of acetyl-acetone cleaved. A reaction scheme was proposed in accordance with the cleavage stoichiometry, suggesting methylglyoxal as second product (Scheme1).

Scheme 1.
Reaction catalyzed by 1,3-dicarbonyl-dioxygenase.

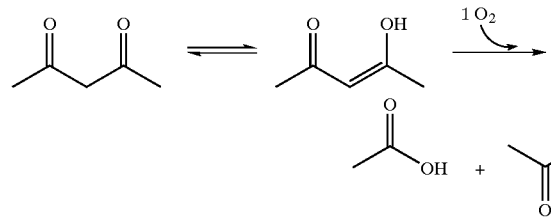

By comparison with purchased methylglyoxal, the two signals could in fact be attributed to the methyl-group of methylglyoxal. The integrals over the 1H-signals also showed, that acetate and methylglyoxal were formed in equimolar amounts. These findings were confirmed by HPLC ($t_{Methylglyoxal}$: 13.1 min, $t_{Acetate}$: 15.4 min, $t_{Acetylacetone}$: 30 min). As the methylglyoxal purchased (40%) had no exact concentration assigned, the methylglyoxal calibration for HPLC was refined by determining the acetate concentration in assays where acetylacetone had been converted, and by defining the respective methylglyoxal peak as equimolar.

As a consequence of the reaction found, we designate the found enzyme as 1,3-dicarbonyl-dioxygenase.

Example 5
Catalytic Requirements and Stability

The native enzyme has no requirements for exogenous cofactors. The absorbance peak of the enzyme showed only the peak due to aromatic amino-acids ($\lambda_{max}$=281 nm) with no distortions or additional absorbance indicative of the presence of non-protein prosthetic groups. The enzyme showed maximum stability at a pH of 7.5–8.0 and a halftime-stability: t=3550 min (0.05 mg/mL protein concentration, 4° C.). The addition of potential stabilizing agents such as glycerol (10%), glucose (12.5%), ascorbate (1 mM), bovine serum albumin (1–20 mg/mL), dithiothreitol (1 mM) and mercaptoethanol (1 mM) did not enhance stability. Cell extract, however did not significantly lose activity when incubated at room temperature for several days.

Example 6
Catalytic Properties

Figure 3:
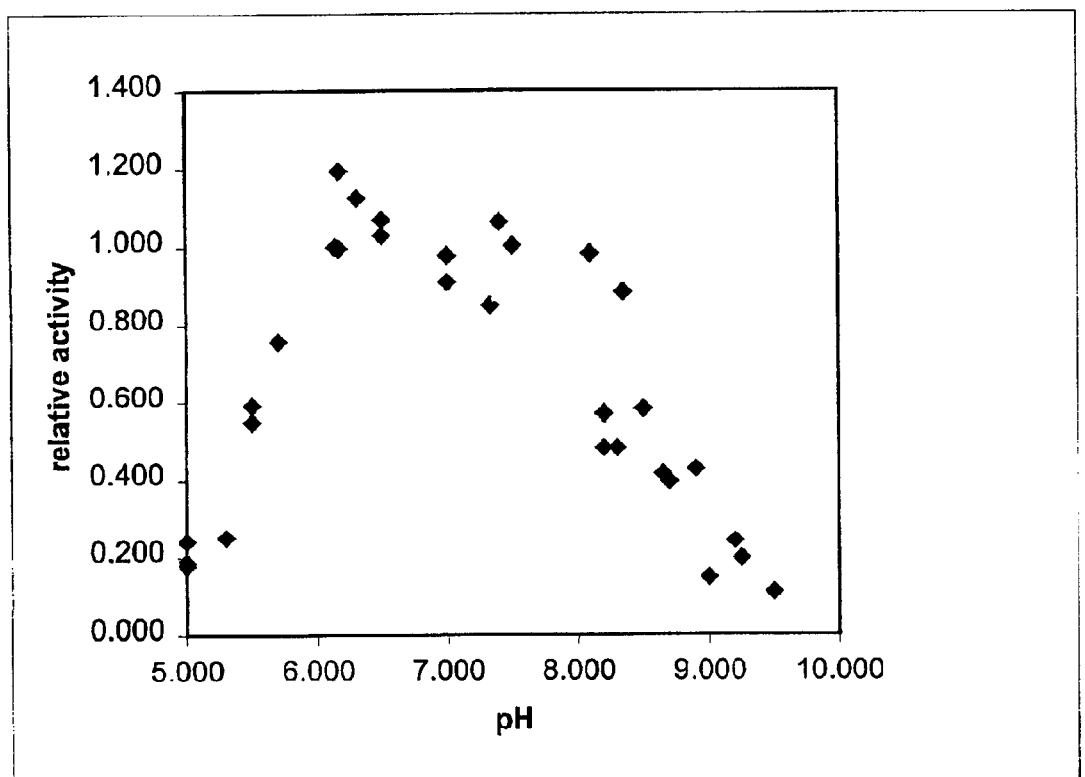
FIG. 3 is a graph illustrating the dependence of enzyme-activity on pH.

The enzyme shows maximum activity at a pH of 6.0–7.5 (FIG. 3). The apparent $V_{max}$ of the purified enzyme has been determined as 10.5 $U/mg_{Enzyme}$. A variation of substrate concentration (0.5–1 mM), had no influence on the apparent $K_{O2}$, which suggests, that neither substrate inhibition nor a putative double limitation of substrate exerted a significant influence on the determination of $K_{O2}$. Similarly, $K_s$ and $v_{max}$ remained constant, when determined at various oxygen-concentrations.

Example 7
Substrate Spectrum

Various diketones and related substances were tested as substrates for the 1,3-dicarbonyl-dioxygenase. The results of these investigations are outlined in Table 3. The apparent Ks and $K_{O2}$ values do however not take into account the real kinetic mechanism. The $K_{O2}$ value, which is estimated from the rate of oxygen depletion and not by initial rate measurement, does not take into account the possible inhibiting effects of product formed.

TABLE 3

APPARENT KINETIC CONSTANTS

| Substrate | $V_{maxrel.}$ | $K_s$ [μM] | $K_{O2}$ [μM] | $O_2$/Substrate |
|---|---|---|---|---|
| Acetylacetone (=Pentan-2,4-dion) | 1.00 | 7.4 ± 1.9 | 38 ± 6 | 1.0 |
| 1-Phenyl-1,3-butandion | 0.15 | 4.5 ± 2* | 100 ± 15 | 1.0 |
| 3-Methylpentandion | 0.25 | 23.1 ± 6.8 | 40 ± 8 | 1.0 |
| 5,5-Dimethylhexan-2,4-dion | 0.25 | 14.2 ± 3.7 | 70 ± 15 | 0.9 |
| 2,4-Octandion | 0.58 | 5.9 ± 1.5 | 85 ± 15 | 1.0 |
| 2,4-Nonanedione | 0.56 | 7.5 ± 2.1 | 112 ± 15 | 1.0 |
| 2-Acetocyclopentanone | 0.52 | 21.0 ± 6.1 | 15 ± 5 | 1.0 |
| 2-Acetocyclohexanone | 0.58 | 18.1 ± 4.2 | 21 ± 5 | 0.9 |
| 2,4-Dioxo-pentanoic-acid-ethyl-ester | 0.09 | 7.4 ± 2* | 91 ± 15 | 1.0 |
| (2-Hydroxyphenyl-)-ethan-1-one | 0.00 | — | — | — |
| 2,4-Dioxo-pentanoic acid | 0.00 | — | — | — |
| 3,3-Dimethylpentane-dione | 0.00 | — | — | — |
| 1,3-Cyclohexanedione | 0.00 | — | — | — |
| 4-Methoxy-3-penten-2-one | 0.00 | — | — | — |

*Ks determined with the oxygen electrode

While aliphatic 1,3-diketones without bulky substituents appear to be good substrates for the 1,3-dicarbonyl-dioxygenase, 5,5-dimethylhexane-2,4-dione, with its bulky tertiary-butyl-group is cleaved at significantly lower rates. Longer unbranched chains, however, do not seem to hinder the enzyme to such a big extent. Also a substitution at C-3, as it is found in 3-Methyl-2,5-pentanedione, as well as in 2-Acetocyclopentanone and 2-Acetocyclohexanone do still allow quite good reaction rated. When C-3 bears two substituents, however no conversion is possible. These finding suggest, that enolization might be a crucial step for conversion. Cyclohexanedione, where the keto-enol-groups are fixed in an E-configuration, is not accepted as a substrate.

Another interesting point is that acetopyruvate is not cleaved by the enzyme, while the ethyl-ester is accepted as a substrate. The negatively charged carboxy-group hinders cleavage. This is consistent with the results from activity-pH-relationship studies. Acetylacetone, having a pKs of 9.0, is accepted by the enzyme only up to a pH of 9. At higher pH-values, the deprotonated, negatively charged acetylacetone is not accepted. Because of these findings, an enol-double-bond in Z-configuration is suggested as the reactive structure. Therefore 3-methoxy-3-pentenone was tested as substrate, it was, however, not accepted. A possible explanation for this phenomenon is that the (acidic) hydroxy-group of the enol-structure is crucial for the binding of the substrate to the enzyme. In the case of 3-methoxy-3-pentenone this hydroxy group is replaced by a methoxy group, which cannot be deprotonized. This assumption, however, must be examined by further experiments.

The cleavage-stoichiometry of several non-symmetrical substrates was also investigated, in order to be able to determine the regiospecificity of the enzyme. This was done by conversion of the respective substrate with partially purified enzyme. Methylglyoxal and acetate formed were measured by HPLC. Remaining substrate was calculated.

TABLE 4

PRODUCTS OF VARIOUS SUBSTRATES; DETERMINED BY HPLC

| Substrate | Acetate % | Methyl-glyoxal % | Substrate % | Methylglyoxal/Acetate |
|---|---|---|---|---|
| Acetylacetone | 50 | 50 | 0 | 1 |
| 1-Phenyl-1,3-butane-dione* | 8 | 68 | 24 | 9 |
| 3-Methylpentanedione | 82 | — | 18 | — |
| 5,5-Dimethylhexane-2,4-dione | 21 | 70 | 9 | 3.3 |
| 2,4-Octanedione | 55 | 27 | 18 | 0.5 |
| 2,4-Nonanedione | 35 | 48 | 17 | 1.4 |
| 2-Acetocyclopenta-none | 90 | — | n.d. | — |

Conversion of substrate (4 mM, 1.6 mM* respectively) at 25° C. in oxygen saturated buffer for one hour.

A discrimination between the two possible sides of attack can be observed, but there is no pronounced regio-selectivity, except for 1-phenyl-1,3-butanedione. This may be due to a steric effect, but it could also be due to the stabilization of 1-phenyl-1,3-butanedione as its conjugated isomer 4-hydroxy-4-phenyl-3-buten-2-on (III) (Scheme 2). If the substrate is cleaved by oxygen-addition to the enol-double-bond, the strong preference for the cleavage reaction resulting in methylglyoxal contrary to the acetate yielding reaction, may be explained.

SCHEME 2.
ISOMERS OF 1-PHENYL-1,3-BUTANEDIONE

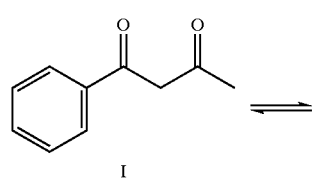

I

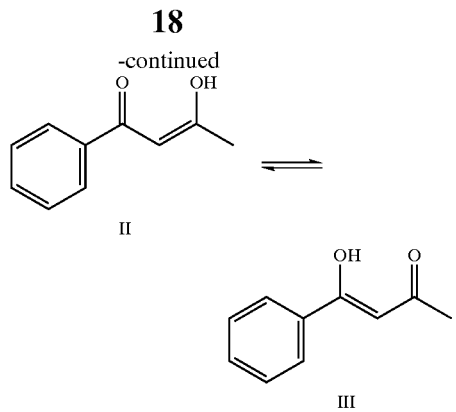

Example 8

Inhibition Studies

The freshly prepared solutions of the respective inhibitors in buffer were added to partially purified enzyme, which then was incubated at room temperature. Activity was measured by the oxygen electrode assay as described previously (25° C., 0.5 mM acetylacetone end-concentration, Tris-buffer, pH 7.5). For reactivation, purified enzyme, which had previously been inactivated by incubation with o-phenantroline (1 mM), was incubated with Tris-buffer (20 mM, pH 7.5) containing the respective metal-salts (5 mM).

TABLE 5

INHIBITION AND REACTIVATION OF 1,3-DICARBONYL-DIOXYGENASE

| | Relative activity [%] | | $C_{Inhibitor}$ | |
|---|---|---|---|---|
| | 2 min | 10 min | [mM] | Group-specificity |
| INHIBITION | | | | |
| p-Hydroxymercurybenzoic acid | 56 | 45 | 2.5 | Cys |
| Iodo-acetic-acid | 100 | 72 | 2.5 | Cys |
| Succinic anhydride* | 62 | 23 | 2.5 | Ser, Thr |
| Diethyl-pyrocarbonate | 18 | 12 | 2.5 | His, Tyr |
| EDAC° | 100 | 95 | 2.5 | Glu, Asp |
| DTNB°° | 88 | 85 | 2.5 | Cys |
| KCN | 41 | 14 | 2.5 | Metal |
| NaN₃ | 54 | 38 | 2.5 | Metal |
| EDTA | 85 | 36 | 1.0 | Metal |
| o-Phenantroline | 38 | 10 | 1.0 | Metal |
| H₂O₂ | 0 | 0 | 0.25 | Metal |
| pH 5.5 | 50 | 30 | — | Metal |
| REACTIVATION | | | | |
| FeSO₄ | 14 | 33 | 5.0 | — |
| FeCl₃ | 0 | 0 | 5.0 | — |
| CoCl₂ | 0 | 0 | 5.0 | — |
| MnSO₄ | 0 | 0 | 5.0 | — |
| ZnSO₄ | 0 | 0 | 5.0 | — |
| NiCl₂ | 0 | 0 | 5.0 | — |
| CuCl₂ | 0 | 0 | 5.0 | — |

°1-Ethyl-3-(3-dimethylaminopropyl)-carbodimide
°°5'-Dithio-bis-(2-dinitrobenzoic acid)
*100 mM dilution of inhibitor in ethanol, addition of 5 μL/200 μL sample.

The data, showing that incubation with Fe(II) partially restores the enzyme-activity, suggest that the enzyme contains Fe(II), which is directly involved in the catalytic mechanism. This could also explain the complete inactivation of the Enzyme by H₂O₂, which can easily oxidize Fe(II)

to Fe(III). Furthermore histidine seems to play an important part. This might also explain the decrease in activity, when the reaction is performed at a pH lower than 6.0 (pKs of histidine). As outlined in Table 5, after incubation at pH's lower than 5.5, activity could not be restored at pH 7.5. A possible explanation might be, that iron is coordinately bound by the nitrogen groups of histidine residues. Acidification leads to protonated nitrogen, which cannot bind iron, which gets lost as a consequence. Metal quantification in the enzyme is in progress. The active center of ring-cleaving extradiol dioxygenases (e.g. catechol 2,3-dioxygenase), catalyzing a similar reaction, but only with aromatic substrates, also contains Fe(II), coordinated by histidine-residues. (The 1,3-dicarbonyl-dioxygenase however does not accept catechol or methylcatechol as substrates).

Example 9

Protein-Sequencing and Cloning of the Sequence

Protein sequencing of the purified protein resulted in 3 peptides sequences:

| | |
|---|---|
| V[I/L]AS[I/L]GWAEAQGAW[I/L]ATK | (SEQ ID NO:5) |
| KGNDD[I/L]FN[I/L]PG[I/L] | (SEQ ID NO:6) |
| NEQEGGSTAYAPSYGFESSQ[I/L]HGK | (SEQ ID NO:7) |

Peptide sequencing was performed using MALDI-T of to identify the respective amino acids by molecular weight; therefore isoleucine and leucine cannot be discriminated. Moreover certain inaccuracies were later found by comparing the peptide data to the deduced amino amino acid derived from cloned DNA sequences, (e.g., SEQ ID NO: 6 is in reverse order and arginine in SEQ ID NO: 7 was later identified as glycylglycine). Degenerate oligonucleotides "a" and "b" (below) were designed based on the underlined portions of SEQ ID NO: 7 and SEQ ID NO: 5, respectively.

```
Forward primer - oligonucleotide a                    (SEQ ID NO:8)
                          A
             A    C    G           T        T      G
     C  G  G  G  G  G  T  A  T  C  C  T  A  T  A  C
5'-AAT GAA CAA GAA GGC GGA TCA ACC GCA TAT GCG CCA TCG TAC GGC TTT GAA-3'

Reverse primer - oligonulceotide b:                   (SEQ ID NO:9)
       G
       C         C    A
     T  G  C  G  C  G
5'-CCA AGC TCC TTG AGC TTC CGC CCA-3'
```

For synthesis of the degenerate oligos, a mixture of nucleotides (as indicated above) was used at wobble positions. Forward primer 'a' (SEQ ID NO: 8) and reverse primer 'b' (SEQ ID NO: 9) gave a 190 bp-PCR-product. Sequencing showed that part of the intermediate region found coded for SEQ ID NO: 6.

The dig-labeled 190 bp PCR-product was used as a probe for southern-blot. A 3 kb-band was found with EcoRI digested chromosomal Acinetobacter DNA. Based on this result, a gene library of 2–4 kb fragments of EcoRI in pBluescript II SK(-) was constructed. The plasmids, which were isolated from this gene library, were used as a template for PCR. Forward primer 2405:

TCTTCAGGTGCATTGCATGG (SEQ ID NO: 10)
and reverse primer 2406:
ACCATGCAATGCACCTGAAG (SEQ ID NO: 11)
were designed based on parts of the sequence of the 190 bp-PCR product. The PCR-reaction was performed with the designed sequence specific primers 2405 or 2406 on the one hand and the vector-specific primers T3 and T7 on the other hand. A 1 kb product (T3/2405) and two identical 2 kb-products (T3/2406 and T7/2406) were amplified from the gene library. They were partially sequenced. An open reading frame was found, coding for a 16.607 kDa protein and containing the 190 bp-sequence (FIG. 4). Upstream of the ORF, putative promotor binding sites as well as a Shine Dalgano-sequence were found in appropriate distances (underlined).

By Blast search with various parameters no homologous proteins were found Highest homology was obtained with a 170 amino-acid protein from Mycobacterium tuberculosis with unknown function (30% identity). No conserved signatures were detected with the Pfam-search program (publicly available through the Washington University in St. Louis, Mo. http website located at pfam.wustl.edu).

Example 10

Over-Expression of the 1,3-dicarbonyl-dioxygenase-gene in pMS470

Figure 5:
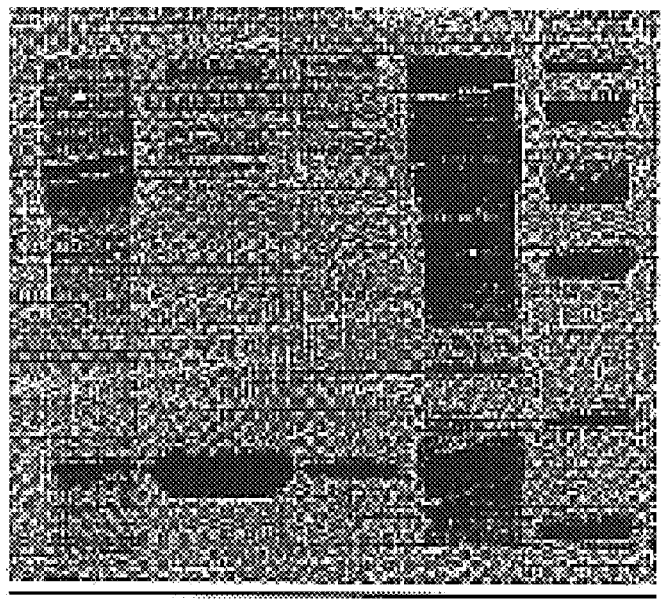
FIG. 5 is a picture of an SDS gel showing the purification of recombinant *A. johnsonii* 1,3-dicarbonyl-dioxygenase.

Recombinant protein was produced as described in "Methods" (supra). FIG. 5 is an SDS gel showing the purification of recombinant protein. Lanes 1 and 4 contain cell-extract from recombinant E.coli expressing 1,3-dicarbonyl-dioxygenase; lane 5 contains a MW-standard, lanes 2 and 3 contain partially purified enzyme (after the Phenyl Sepharose™ column). The resulting cell extract (lanes 1 and 4) shows an over-expression-band at 16.6 kDa.

Recombinant enzyme was purified over two columns with the standard procedure and showed elution properties which are identical with those of the wild-type-enzyme. Molecular weight determination showed that the enzyme is a homotetramer.

TABLE 6

PURIFICATION PROCEDURE OF THE RECOMBINANT PROTEIN

| Fraction | Volume | Activity [μmol/min/mL] | Protein concentration [mg/mL] | Protein [mg] | Units/ mg$_{Protein}$ |
|---|---|---|---|---|---|
| Cell-extract | 20 | 30 | 49 | 980 | 0.6 |
| First column | 50 | 25 | 3.6 | 180 | 6.9 |
| Second column | 20 | 14 | 1 | 20 | 14 |

The substrate acceptance of the recombinant protein was also comparable to that of wild-type enzyme, as can bee seen in Table 7.

TABLE 7

RELATIVE ACTIVITY OF WILD-TYPE ENZYME AND RECOMBINANT PROTEIN AT NON-LIMITING SUBSTRATE CONCENTRATIONS

| Substrate | $V_{max\ clone}$ | $V_{max\ wild-type}$ |
|---|---|---|
| Acetylacetone(=Pentane-2,4-dione) | 1.00 | 1.00 |
| 1-Phenyl-1,3-butanedione | 0.08 | 0.05 |
| 3-Methylpentanedione | 0.85 | 0.83 |
| 5,5-Dimethylhexane-2,4-dione | 0.08 | 0.05 |
| 2,4-Octanedione | 0.60 | 0.50 |
| 2,4-Nonanedione | 0.25 | 0.30 |
| 2-Acetocyclopentanone | 0.43 | 0.31 |
| 2-Acetocyclohexanone | 0.48 | 0.56 |
| 2,4-Dioxo-pentanoic-acid-ethyl-ester | 0.08 | 0.10 |
| (2-Hydroxyphenyl-)-ethane-1-one | — | — |
| 2,4-Dioxo-pentanoic acid | — | — |
| 3,3-Dimethylpentanedione | — | — |
| 1,3-Cyclohexanedione | — | — |
| 4-Methoxy-3-penten-2-one | — | — |

Example 11

Conclusion

The enzyme found catalyzes a novel oxygenolytic reaction of various aliphatic diketones without exogenous cofactor requirement. It has no pronounced regio-selectivity, which suggests that substrates with longer alkyl-substituents on both sides could also be accepted. Moreover, a catalytic mechanism involving histidine and Fe(II) is suggested by this work. However, no similar sequences have been found by BLASTX-search.

Although the present invention and its advantages have been described in detail, it should be understood that various changes, substitutions and alterations can be made herein without departing from the spirit and scope of the invention. Moreover, the scope of the present application is not intended to be limited to the particular embodiments of the process, manufacture, composition of matter, means, methods and/or steps described in the specification. As one of ordinary skill in the art will readily appreciate from the disclosure of the present invention, processes, manufacture, compositions of matter, means, methods, or steps, presently existing or later to be developed that perform substantially the same function or achieve substantially the same result as the corresponding embodiments described herein may be utilized according to the present invention. Accordingly, the invention is intended to include within its scope such processes, manufacture, compositions of matter, means, methods, or steps.

REFERENCES

All the references cited in the foregoing specification are incorporated herein by reference in their entirety.

What is claimed is:

1. An isolated polynucleotide encoding a subunit of an enzyme exhibiting 1,3-dicarbonyl-dioxygenase activity, said polynucleotide comprising a nucleotide sequence selected from the group consisting of:
   (a) a nucleotide sequence encoding the amino acid sequence set forth in SEQ ID NO:2; and
   (b) the nucleotide sequence set forth in SEQ ID NO: 1.

2. An isolated polynucleotide, said polynucleotide consisting of a nucleotide sequence encoding a subunit of a 1,3-dicarbonyl-dioxygenase enzyme or a complementary strand of said nucleotide sequence, said subunit consisting essentially of an amino acid sequence that has at least 90% identity to SEQ ID NO:2, with the proviso that any histidine residue in SEQ ID NO:2 remains invariant.

3. The isolated polynucleotide of claim 2, with the further proviso that any tyrosine, serine and threonine residue remains invariant.

4. The isolated polynucleotide of claim 2, with the further proviso that any cysteine residue remains invariant.

5. The isolated polynucleotide of claim 2, with the further proviso that any amino acid substitution to SEQ ID NO:2 is conservative.

6. The isolated polynucleotide of claim 2, said amino acid sequence having at least 95% identity to SEQ ID NO:2.

7. The isolated polynucleotide of claim 2, said polynucleotide containing:
   (a) the nucleotide sequence set forth in SEQ ID NO:3;
   (b) the nucleotide sequence set forth in SEQ ID NO:4;
   (c) the nucleotide sequence set forth in SEQ ID NO:8;
   (d) the nucleotide sequence set forth in SEQ ID NO:9;
   (e) the nucleotide sequence set forth in SEQ ID NO:10; or
   (f) the nucleotide sequence set forth in SEQ ID NO:11.

8. An isolated polynucleotide consisting of a nucleotide sequence selected from the group consisting of:
   (a) the nucleotide sequence set forth in SEQ ID NO:1
   (b) the nucleotide sequence set forth in SEQ ID NO:3;
   (c) the nucleotide sequence set forth in SEQ ID NO:4;
   (d) the nucleotide sequence set forth in SEQ ID NO:8;
   (e) the nucleotide sequence set forth in SEQ ID NO:9;
   (f) the nucleotide sequence set forth in SEQ ID NO:10;
   (g) the nucleotide sequence set forth in SEQ ID NO:11; and
   (h) a nucleotide sequence that is complementary to a nucleotide sequence of (a)–(g).

9. A nucleic acid vector comprising a nucleotide sequence of claim 2.

10. The vector of claim 9 wherein the nucleotide sequence is operably linked to a promoter.

11. A host cell containing the vector of claim 9.

12. A process for producing a subunit of an enzyme exhibiting 1,3-dicarbonyl-dioxygenase activity, the process comprising the steps of:
   (a) culturing a host cell of claim 10 under conditions sufficient for the cell to produce the subunit, and
   (b) isolating the subunit from the cell culture.

13. The process of claim 12 wherein the enzyme-expressing cell is a prokaryotic cell.

14. The process of claim 13 wherein the prokaryotic cell is an *Acinetobacter johnsohnii* cell.

15. A process for producing an enzyme exhibiting 1,3-dicazbonyl-dioxygenase activity, the process comprising the steps of:
   (a) culturing a host cell of claim 10 under conditions for the sufficient for the cell to produce the enzyme, and
   (b) isolating the enzyme from the cell culture.

* * * * *